United States Patent
Zhao

(10) Patent No.: US 6,605,305 B2
(45) Date of Patent: Aug. 12, 2003

(54) PLANT DRUG FOR TREATMENT OF LIVER DISEASE

(76) Inventor: Xinxian Zhao, 67-08 168th St., Flushing, NY (US) 11365

( * ) Notice: Subject to any disclaimer, the term of this patent is extended or adjusted under 35 U.S.C. 154(b) by 14 days.

(21) Appl. No.: 09/824,916

(22) Filed: Apr. 4, 2001

(65) Prior Publication Data

US 2003/0026854 A1 Feb. 6, 2003

(51) Int. Cl.$^7$ ................................................ A61K 35/78
(52) U.S. Cl. ........................................... 424/725
(58) Field of Search .......................... 424/725

*Primary Examiner*—Christopher R. Tate
*Assistant Examiner*—Randall Winston

(57) ABSTRACT

The present invention related to safe plant drug for treatment of liver disease, specifically, this invention proves a safe plant drug Schisandrin and its preparation. Schisandrin has the following pharmaceutical functions: increasing tumor suppresson genes express activity, decreasing activity of oncogenes, increasing immune function, increasing liver DNA synthesis, decreasing serum alamine aminotransferase activity, increasing glutathione level, increasing glutathione reductase activity, decreasing lipid peroxidation of liver, increasing hepatic microsomal monooxygenases activity, increasing ATP content in liver, increasing energy metabolism activity, decreasing density lipoprotein oxidation, protecting gastrointestinal function, increasing killer cell activity, increasing complement activity, decreasing induced liver cancer activity and decreasing grown of cancer cells.

1 Claim, No Drawings

PLANT DRUG FOR TREATMENT OF LIVER DISEASE

BACKGROUND OF THE INVENTION

The present invention related to safe plant drug for treatment of liver disease, specifically, this invention proves a safe plant drug Schisandrin and its preparation.

DESCRIPTION OF THE PRIOR ART

The most common types of liver disease are hepatitis and cirrhosis. So far, no one drug has been succeeded to treat for hepatitis and cirrhosis. The hepatitis victim is always short on appetite and finds it is difficult. Therefore, it is important that to eat the suitable food to supply liver for self-repair. The traditional medical book described that a good treatment for hepatitis is high protein diet, Brewer's yeast, wheat germ, egg yolks, and other high quality protein, which combats the stress damage. Some drugs have been used for treatment of liver disease, but clinical results are not successful.

For the reasons given above, to discover an effect safe drug for treating patients with liver disease is necessary and important.

DETAILED DESCRIPTION OF THE INVENTION

Liver is the largest organ of the human body. It has about 500 recognized functions. The liver makes its own enzymes acted as catalysis and adjustment of major metabolism and energy of human body. There are 70,000 new cases of hepatitis reported annually in the United States, but these figures represent only a small part of the actual number of cases.

Infections hepatitis, contracted by eating tainted foods or water, or inhaling airborne virus from infected individuals. Serum hepatitis is spread by transfusions of contaminated blood and by injections with unsterilized hypodermic needles. When hepatitis does occur, the first classic symptom is a gradually increasing weakness and dizziness which may seem to be the first stages of flu or a bad cold. Therefore, many patients with early hepatitis lost good opportunity for treatment. After that the virus acts to destroy the tissue of the liver and interferes with the liver's ability to process waste materials of the body and caused nausea, pains in the stomach, tenderness and swelling in the area of the liver and an unconquerable loss of appetite. Hepatitis and alcoholism will be developed to chronic hepatitis and cirrhosis. Chronic hepatitis, which lasts for more than three months (some cases have been known to last up to two years), is considered more dangerous than acute cases of hepatitis since longer bouts of the disease can very easily turn into cirrhosis, a disease with a high fatality rate. Cirrhosis of the liver is the cause of 32,000 deaths annually and it is now among the ten leading causes of death in the United States. Hepatitis has several types. Recently, hepatitis A, B and C caused serious problems. The hepatitis C virus (HCV) is one of the major causes of liver disease. Nearly 4 million people in the United States have antibodies to HCV, which indicates at least previous exposure to the disease if not active infection. Acute infections can develop into chronic hepatic disease, including cirrhosis, liver failure, and liver cancer. About 20% of those infected develop cirrhosis after 10 years or more of infection. Chronic infection leading to liver failure accounts for many of the liver transplants performed in the United States. Many researchers believe that HCV is the most common cause of primary liver cancer in the developed world.

The present invention disclosed that a new safe plant drug for treatment of liver disease, specifically, this invention proves a safe plant drug Schisandrin and it preparation. The following specific examples will provide detailed illustrations of methods of producing relative drugs, according to the present invention and pharmaceutical dosage units containing demonstrates its effectiveness in treatment of liver disease. These examples are not intended, however, to limit or restrict the scope of the invention in any way, and should not be construed as providing conditions, parameters, reagents, or starting materials which must be utilized exclusively in order to practice the present invention.

EXAMPLE 1

Chemical and Physical Information a. Molecular formula: $C_{28}H_{34}N_9$
b. Molecular weight: 514.55
c. Physical data:
mp: 97–99° C.
$[\alpha]_D^{20}$ –50 (C=1.12, $CCl_4$)
UV$\lambda_{max}$ nm(logε): 221 (4.69), 260 (sh) (4.01), 295 (sh.) (3.42);
IR$\nu_{max}^{KBr}$ $cm^{-1}$: 3540 (OH), 1715, 1700, 1640, 1600, 1505, 1352, 1235;
MS m/e: 514 ($M^+$), 431, 415;
NMR ($CCl_4$) δ: 6.72 (1H, 4-H), 6.30 (1H, 11-H), 5.70 (1H, 6-H), 1.78 (1H, 8-H), 3.80, 3.68 3.56 and 3.40 (4×3H, 4×$OCH_3$), 5.82 and 5.78 (2×1H, $OCH_2O$), 1.46 (1H, OH), 1.16 (3H, 7-$CH_3$), 1.04 (3H, J=7, 8-$CH_3$), 2.00~2.50 (2H, $CH_2$), 1.78 (3H, J=7, J=1.5, =C—$CH_3$), 5.80 (1H, =CH ($CH_3$)), 1.30 (3H, J=1.5, O=C—C—$CH_3$).

d. Chemical structure of Schisandrin (SCS) is shown as below.

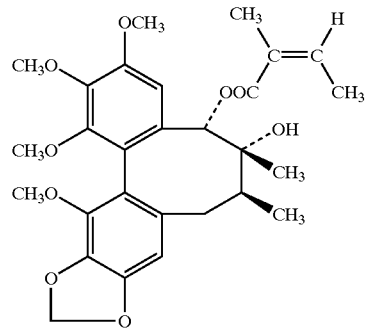

EXAMPLE 2

Manufacturing Process, Extraction and Purification of SCS

Dried powder of the fruit of Schisandra chinensis (Turcz) Baill or Schisandra sphenanthera Rehd was added to water. The mixture was heated to boil and simmred for 1.5 hours after boiling. This mixture was filtered. The powder residue extracted with 80% of ethanol. The ethanol was recovered and still residue was obtained. The still residue extracted with 80% of ethanol-gasoline (1:1). Ethanol layer was saved. Ethanol layer was concentrated under reduced pressure. Crude crystalline was obtained. The crystalline dissolved in benzene. The mixture was filtered and benzene was saved. The benzene was recovered and still residue recrystallized in ethanol. The crystalloid maternal solution of recrystalline was saved and dried under reduced pressure. The dried powder was obtained and passed through a column packed with $Al_2O_3$ and elute with petroleum ether, petroleum ether-benzene (1:1) and benzene-methyl alcohol (1:1). Fraction of petroleum ether-benzene (1:1) was collected and concentrated under reduced pressure. The crystalline was obtained and recrystallized out from methyl alcohol and then recrystallized out from petroleum ether-benzene. The crystalline is Schisandrin.

EXAMPLE 3

Manufacture of SCS Preparation

SCS powder granulated accorded to the conventional granulation method. The mixture content decreased from 100% to 93%. The 7% of content was different types of fillers. Disintegrants, lubricants and glidants were used: microcrystalline cellulose (Avicel PH 105, PH 101, PH 102, PH 200, all from FMC Corp., Lehmann and Voss and Co., Hamburg, Germany; and Vivacel 200, Rettenmaier and S öhne GmbH, Ellwangen-Holzmühle, Germany), microfine cellulose (Elcema P 050, P 100, G 250, all from Degussa AG, Frandfurt, Germany; and Tablettierhilfsmittel K, Merck KGaA, Darmstadt, Germany), lactose cellulose granulate (Cellactose, Meggle, Wasserburg, Germany), α-lactose monohydrate (Lactose D 80, Meggle, Wasserburg, Germany), and modified maize starch (Starch 1500, Colorcon GmbH, Königstein, Germany).

The disintegrants tested were the following: cross-linked sodium carboxymethyl cellulose (Ac-Di-Sol, FMC Corp./Lehmann and Voss and Co.; and Nymcel ZSB 10, Nymcel ZSB 16, METSÄ-SERLA, Njimegen, Netherlands), Cross-linked calcium carboxymethyl-cellulose (ECG 505, FMC Corp./Lehmann and Voss and Co.), potato starch (Caeleo, Hilden, Germany), sodium starch glycolate (Explotab, Gustav Parmentier, Frankfurt, Germany; and Primojel, AVEBE Deutschland, Düsseldorf, Germany), cross-linked polyvinylpyrrolidone (Kollidon CL, BASF AG, Ludwigsburg, Germany; and Polyplasdone XL, ISP Deutschland, Frechen, Germany), and low-substituted hydroxypropyl-cellulose (L-HPC LH 22, L-HPC LH 31, both from Shin-Etsu Chemical Co., Ltd., Tokyo, Japan).

For lubrication, the following were used: magnesium stearate (Otto Bärlocher GmbH, Munich, Germany), glyceryl tristearate (Dynasan 118, Hüls Ag, Witten, Germany), and polyethylene glycol (PEG 6000, Hoechst AG Frankfurt/Main, Germany).

As glidants, colloidal silicon dioxide (Cab-O-Sil M 5, Cabot GmbH, Hanau, Germany; Syloid 244, W. R. Grace and Co., Lexington, Ky., and Aerosil 200, Degussa AG, Frankfurt/Main, Germany) and hydrophobic colloidal silicon dioxide (Aerosil R 972, Degussa AG) were used. As a stabilizer, ascorbic acid (Merck KGaA, Darmstadt, Germany) was added.

The content of SCS was kept constant at a level of 100 mg per tablet. Tablet weight was varied between 100–105 mg. Tablet mixtures were mixed for 10 min in the Turbula mixer (type T2C, Willy Bachofen, Basel, Switzerland). The n lubricants were sieved through a 315-μm sieve into the mix. Final mixing was carried out for 5 min at 42 rpm in the Turbula mixer. The mixtures were compressed using a rotary press (Korsch PH 103, Korsch, Berlin). The lower compression roller was instrumented with four strain gauges (type 3/120 LY 11, Holtinger Baldwin, Inc., Darmstadt, Germany). A Philips carrier-frequency bridge (PR 9307 Philips, Kassel, Germany) was used for signal amplification. Each batch was compressed at different levels of compression force in the range of 1 to 25 kN. As a stabilizer, ascorbic acid (Merk KGaA, Darmstadt, Germany) was added. Sugar-coating operation was also performed conventionally.

EXAMPLE 4

Assay and Identify of SCS

SCS was identified by melting point determination, UV, IR, NMR, Mass spectroscopy and chromatographic behavior. The base was recrystallised from petroleum ether-benzene to give pure ingredient, mp 97~99° C. The $UV^{EtOH}$ nM (log ε): 221 (4.69), 260 (4.01), 295 (3.42). The $IRv^{KBr}$ $cm^{-1}$: 3540 (OH), 1715, 1700 (COOH), 1640, 1600, 1505 (benzene), 1352, 1235.

The content of SCS was determined by reversed phase high performance liquid chromatography. The HPLC system consisted of Alltech $C_{18}$ column (250 mm×4.6 mm), mobile phase of methanol-water (81:19) mixture, with detection at 240 nm, flow rate 1.5 mL/min and column temperature 25° C. The linear ranges of determination of SCS was 0.081 ~0.729 μg (r=0.9999). The mean recovery of 100% for SCS is obtained. The method is very sensitive, rapid and accurate.

EXAMPLE 5

Pharmacology Information

SCS is a pure ingredient which extracted from Chinese medical herb: *Schisandra chinensis Baill* or *Schisandra sphenanthera Rehd* or *Schisandra henryi Clarke*. SCS has been used as tonic and an anti-aging drug in traditional Chinese medicine. Above herb has adaptogenic properties increase resistance to a wide range of physical, chemical, and emotional stresses while promoting improved overall regulation of physiological processes. Recently, SCS has been used as a drug for treatment of liver disease in China. For example, SCS has active against viral and chemical induced hepatitis, decreasing SGPT levels in patients with viral hepatitis, normalizing liver function, inhibiting carbon tetrachloride induced lipid peroxidation, inducing effect on the cytochrome P-450 enzyme system, increasing liver protein DNA, RNA, protein and glocogen synthesis and inhibiting oncogenes. The following sections will be described relative pharmacological effects of SCS.

EXAMPLE 6

Effect of SCS on Tumor Suppressor $p^{53}$ of Cancer Cells

The recent progress made in molecular genetics has revealed that $p^{53}$ gene is a tumor suppressor gene. Disorder of mutations of $p^{53}$ plays a very important role in the development of many cancers. $^{17}p$ allelic and $p^{53}$ mutations appears to be the most common genetic abnormalities in cancer including in the development of cancer. However, determinate tumor suppressor of cancer cells is very difficult and experimental errors are lager. The present invention proved a new and easy method for determinate tumor suppressor of cancer cells.

Methods

The leukemic cancer cells and normal cells were cultured in RPMI 1640 medium supplement with 10% fetal bovine serum. All the exons of the $p^{53}$ gene were amplified by the polymease chain reaction (PCR) using specific oligonucleotide primers. The PCR products were subjected to single-strand conformation polymorphism (SSCP) analysis. A second PCR-SSCP analysis was performed to ensure that the results were reproducible in each experiment, which showed mobility. Levels of DNA methylation were determined.

Results

TABLE 1

The effect of Drug on $p^{53}$ mutations

| Group | Frequency of $p^{53}$ mutations (%) | P |
|---|---|---|
| Normal gastric cells | 0 | — |
| Gastric cancer cells (no drug) | 35 | — |
| Gastric cancer cells treated by SCS | 10 | <0.01 |

A combination of different molecular genetic analysis is a highly sensitive method for analysis of genetic abnormalities. Data of table 3 showed that SCS could obviously inhibit levels of $p^{53}$ mutations of cancer cells. It means that SCS could increase function of tumor suppressor. Increased tumor suppressor could treat and prevent cancer.

EXAMPLE 7

Effect of SCS on Regulation of Oncogenes

In the present study, the effect of SCS on oncogenes was examined.

Methods

Human myeloblastic leukemic cells (ML-1) were maintained in suspension culture in RPMI 1640 medium supplemented with 7.5% heat-inactivated FBS. Cells growth and viability were assayed by hemocytometer using trypan-blue dye exclusion.

RNA was isolated by the CsCl gradient modification. RNA pellets were washed twice by reprecipitation in ethanol and quantitated by absorbency at 260 nM. RNA analyzed by electrophoresis of 15 μg of RNA through 1.2% agarose formaldehyde gels followed by northern blot transfer to nitrocellulose.

Single-standard uniformly labeled DNA probes were prepared. Probe of c-myc was a 1.7 Kb cla-Eco RI restriction fragment containing the 3'exon region of human c-myc and probe of c-myb was 1.0 Kb myb-specific Bam HI fragment. Probes for n-ras contained DNA fragments using a modification of the PCR technique. Probes for myb, myc and n-ras were isolated. The isolated fragments were labeled to high specific activity with $[\alpha^{32}P]$-dCTP (3000 ci/mmol).

Prehybridization of the filter was performed. The hybridization mixer contained 50,000 cpm of probe. The probes were hybridized at 58° C. in 15 mM NaCl, 1.5 nM sodium citrate for 3 hours. After hybridization, they were exposed to XAR-5 film. Oncogene expression was quantitated by densitometer scanning of the autoradiography. The results are summarized in the tables as below

TABLE 2

The effect of SCS concentration on inhibition of oncogenes

| SCS concentration | Inhibition (%) | |
|---|---|---|
| (ng/ml) | c-myb RNA | c-myc RNA |
| 0 | 0 | 0 |
| 10 | 65.0 ± 5.7 | 70.5 ± 8.5 |
| 50 | 67.7 ± 6.8 | 70.8 ± 8.9 |

This study indicated that SCS could significantly inhibit oncogenes of cancer cells. Cancers would be suitable targeted for gene-directed therapy and the present study has been directed toward the suppression of oncogene activity in cancers. Cellular oncogenes encode proteins have important function in differentiation of cancer cells. The principal functions of c-myc are the induction of proliferation and the inhibition of terminal differentiation in many cells. Overexpression of myc commonly occurs in a wide range of tumors.

EXAMPLE 8

Effect of SCS on Liver DNA Synthesis

It is known that liver injuries induced by hepatotoxic chemicals such as $CCl_4$. $CCl_4$ induced hepatocellular injury by producing $CCl_3$ free radicals. In this study, we investigated the effect of SCS on DNA synthesis in liver of rats.

Methods

Female Balb/c mice (22–24 g) were maintained at 20° C. and a 12 hours light/dark cycle. The food and water allowed adliboti. Mice were randomly assigned to groups of 20 individuals. Twenty-four hours after the last dosing, animals were administered an oral dose of $CCl_4$ (1%, v/v, in olive oil) at 1.0 mmol/kg. In treatment group, mice were treated intragastrically with SCS at daily dose of 50 mg/kg for 4 days. Control animals were given the vehicle (i.e. olive oil, 1 mL/kg). Twenty-four hours after intoxication, heparinized blood samples were drawn from ether-anesthetized mice by cardiac puncture, and the animals were killed by cardiac excision thereafter.

[$^3$H] thymidine (10 μCi/100 g body weight) was injected intraperitoneally and mice were killed 2 hours after the infection. Mice were killed at 12, 24, 36, 48, 72 and 120 hours and their livers were removed.

DNA synthesis was determined by the incorporation of [$^3$H] thymidice into the acid-insoluble fraction. The liver was homogenized in 4 volumes of distilled water. Two ml of homogenate were added to an equal volume of 10% trichloroacetic acid (TCA) solution and centrifuged at 900 g for 10 minutes. The resultant pellet was washed with 5% TCA twice and suspended again in 2 ml of 5% TCA solution. The suspension was incubated at 90° C. for 20 minutes and centrifuged at 900 g for 10 minutes. One ml of the supernatant was put into a scintillation vial and 10 ml of a toluene-based scintillation fluid containing DPO (0.4%), POPOP (0.01%), and Triton X-100 (30%) as added. The radioactivity was counted in a Packard Tri-Carb Liquid scintillation counter. The DNA content of the supernatant was assayed by the method of using calf thymus DNA as the standard.

Results

TABLE 3

Effect of SCS on DNA synthesis of liver

| Group | DNA synthesis (cpm/mg DNA) | | | |
|---|---|---|---|---|
| | 12 h | 24 h | 48 h | 72 h |
| Control | 1220 ± 135 | 1800 ± 195 | 2500 ± 260 | 1780 ± 190 |
| Treatment | 6520 ± 678* | 12305 ± 1405* | 8910 ± 920* | 9300 ± 940* |

*$P < 0.001$, compared with control group

Data of Table 3 shows that DNA synthesis of liver is obviously increased by SCS. These results suggest that SCS accelerated liver regeneration of on mice acute hepatic injury by $CCl_4$.

EXAMPLE 9

Effect of SCS on Enzymes (1)

Recent our studies have demonstrated that SCS could induce drug's metabolizing enzymes in liver of animals, inhibit peroxidation of microsomal membrane lipids and increase activities of superoxide dismutase. In the present study, the effect of SCS on the activities of hepatic enzymes was examined in mice with or without $CCl_4$ intoxication.

Methods

Animal section described as previously. Plasma was obtained by centrifugation. The whole blood at 2000×g at 4° C. Serum alamine aminotransferase (ALT) activity was determined by assay kit from Sigma Chemical Co.

The rats were starved overnight before decapitation. The livers were perfused in situ with ice-cold 1.15% KCl solution. Tissue homogenate was prepared by homogenizing 1 g of hepatic tissue sample in 10 mL ice-cold homogenizing buffer with two 10-secbursts of atissue disintegrator at 135,000 rpm. Hepatic mitochondrial fraction was prepared by differential centrifugation in isotonic buffer (0.25 mM sucrose, 0.1 mM EDTA, 5 mM Tris, pH 7.4).

Glutathione S-trasferase (GST) was determined. Total GST activity in the 105000 g supernatants of the liver homogenate was measured in 100 mM postassium-phosphate buffer (pH 6.5) containing 1 mM glutathione and 1 mM 1-chloro-2, 4-dinitrobenzene.

Results

The experimental data are shown as the following table.

TABLE 4A

Effect of SCS on ALT

| Group | ALT (X ± S) (U L$^{-1}$) |
|---|---|
| Normal | 40.80 ± 5 |
| Control ($CCl_4$) | 560.0 ± 58* |
| Treatment ($CCl_4$ + SCS) | 68.8 ± 7.0** |

*$P < 0.001$, compared with normal group
**$P < 0.001$, compared with control group

TABLE 4B

Effect of SCS on GST

| Group | GST activity ($\mu$mol/mg protein) |
|---|---|
| Normal | 2.50 ± 0.26 |
| Control | 5.85 ± 0.60* |
| Treatment | 2.60 ± 0.28** |

*$P < 0.01$, compared with normal group
**$P < 0.01$, compared with control group $CCl_4$ treatment caused liver damage in mice and increasing in serum ALT activity obviously. The data of table 3 indicated that SCS markedly decreased ALT activity. The $CCl_4$ toxicity was decreased to 87.9% by SCS. The data of Table 4 indicated that SCS markedly decreased GST activity. The inhibition is 55.5%. It means that SCS has protective effect of on mice acute hepatic injury by $CCl_4$.

EXAMPLE 10

Effect of SCS on Enzymes (2)

Methods

The experiments of animal and livers were performed as previously described. Glutathione (GSH) level was determined by an HPLC method. In the present study, the effect of SCS on GHS and GRD were examined.

Results

The experimental data show as the following table.

TABLE 5

Effect of SCS on GSH and GRD

| | GSH (nmol/mg protein) | GRD (mU/mg protein) |
|---|---|---|
| Normal (Norn-$CCl_4$) | 15.6 ± 1.4 | 34.8 ± 3.5 |
| Control ($CCl_4$) | 3.4 ± 0.40* | 14.6 ± 1.8* |
| Treatment ($CCl_4$ + SCS) | 21.8 ± 2.0** | 50.6 ± 6.0** |

*$P < 0.01$ compared with normal group
**$P < 0.001$ compared with control group After $CCl_4$ intoxication, the hepatic mitochondrial GSH level was markedly decreased by 78%. SCS was remarkably increased GSH level in $CCl_4$-treated mice. GSH level of treatment group is much higher than normal group. GSH has broad biological activities and plans an important role in cellular antioxodant effects. GRD catalyzed GSH regeneration from its oxidized form. SCS significantly increased GRD activity. T/C is 347% and T/N is 145%. It means that SCS has protective effect of on mice acute hepatic injury by $CCl_4$.

EXAMPLE 11

Effect of SCS on Peroxidation

It is known that SCS can stimulate DNA synthesis and proliferation of liver cells'decrease the elevated ALT and GST, and inhibit lipid peroxidation.

Methods

The experiments were performed as previously described.

In the present study, the effect of SCS on lipoperoxides was examined.

Results

TABLE 6

Effect of SCS on peroxidation

Lipoperoxides (mmol MDA/g liver protein)

| Group | 1 h | 3 h | 6 h | 12 h | 24 h |
|---|---|---|---|---|---|
| Control | 0.80 ± 0.09 | 0.90 ± 0.09 | 1.1 ± 1.0 | 1.3 ± 1.2 | 2.2 ± 2.0 |
| Treatment | 0.70 ± 0.07* | 0.65 ± 0.069** | 0.60 ± 0.70** | 0.52 ± 0.60** | 0.50 ± 0.58** |

*$P < 0.05$ compared with control group
**$P < 0.01$ compared with control group It is known that the pathogenesis of $CCl_4$-induced hepatic damage involved reactive oxidant species increasing from the metabolism. The liver injure caused by $CCl_4$ is due to theformation of a reactive toxic metabolite by the hepatic cytochrome P-450 system. As data of Table 6 indicated that lipoperoxides are obviously increased in 1, 3, 6, 12 and 24 hours.

EXAMPLE 12

Effect of SCS on Hepatic Microsomal Monooxygenases

As mentioned above section, the SCS markedly decreased lipoperoxides. T/C was 87% (1 h), 72% (3 h), 55% (6 h), 40% (12 h) and 22% (24 h). It means that SCS could obviously protected injury, which caused by $CCl_4$.

In the present study, the effect of SCS on the activities of hepatic microsomal monooxygenases was examined.

Methods

Microsomal preparations—the microsomes used were prepared from rat's liver. The liver was thoroughly perfused in situ with more than 200 ml of 0.9% NaCl solution. The liver was excised, and homogenized with 4 volumes of isotonic (1.15%) KCl solution in a Potter glass homogenizer. The homogenate was centrifuged at 12,000×g for 25 minutes in a refrigerated centrifuge, and the precipitate was discarded. The microsomes were sedimented by centrifugation at 78,000×g for 90 minutes in a Hitachi model 40P preparative ultracentrifuge. The firmly packed pellet of microsomes was resuspended in isotonic KCl solution with the Potter homogenizer and again centrifuged as above. The washed microsomes were finally suspended in isotonic KCl, usually at a concentration of 10 mg of protein per ml. The resultant microsomal suspensions were stored at 4° C. and used within 2 to 3 days. In these preparations isotonic KCl was employed, instead of the more usual 0.25 M sucrose, so as to minimize the adsorption of hemoglobin on microsomes. The microsomal preparations thus obtained were found to be practically free of adsorbed hemoglobin, when examined by zone electrophoresis.

Results

The experimental data are shown as the following table.

TABLE 7

Effect of SCS on monooxygenases

| Group | Cytochrome P-450 (nmol/mg protein) | NADPH-cytochrome Creductase (nmol/mg protein) | Aminopyrine demethylase (nmol HCHO/mg protein) | Benzpyrene hydroxylase (nmol/mg protein) |
|---|---|---|---|---|
| Control | 1.20 ± 0.13 | 120.8 ± 13 | 80.5 ± 9.0 | 20.8 ± 22 |
| Treatment | 2.80 ± 0.30 | 202.5 ± 22 | 180.0 ± 20 | 51.8 ± 6.5 |

The data of Table 7 indicated that SCS increased the hepatic microsomal P-450, NADPH-cytochrome C, reductase aminopyrine demethylase, and benzopyrene hydroxylase activities. Above results suggested that SCS induced monooxygenases. It means that SCS has a protective effect of acute hepatic injury.

EXAMPLE 13

Effect of SCS on Energy Metabolism

It is knows that the ATP provided by the transport of electrons in respiratory chain. Cellular respiration means the use of oxygen in metabolic reactions in the cell. Therefore, regulation of ATP and oxygen consumption is important for energy metabolism.

SCS may effect regulation of energy metabolism including increasing ATP concentration and net synthesis of ATP, and oxygen consumption.

In present study, the effect of SCS on ATP and oxygen consumption was examined. The experiments of animal and livers were performed as previously described.

Results

The experimental data are listed as the following table.

TABLE 8

Effect of SCS on mitochondrion oxygen consumption

| Group | RCR[b] |
|---|---|
| Control (TET[a] 5 μl/L) | 7.90 ± 0.80 |
| Treatment TET + SCS (100 μmol/L) | 12.5 ± 1.10* |

[a]TET: tetrahydrofuran
[b]RCR: respiratory control ratio
*$P < 0.01$ compared with control group

TABLE 9

Effect of SCS on ATP

| Group | ATP (100 μmol/L) |
|---|---|
| Control[a] | 25.8 ± 3.20 |
| Treatment[b] | 35.8 ± 4.0* |

[a]TET (5 μl/L);
[b]TET + SCS (100 μmol/L)
*P < 0.01 compared with control group Table 8 suggested SCS could increase the respiration control ratio. Table 9 suggested SCS could increase ATP concentration. The data of Table 8 and 9 show that SCS can improve energy metabolism and maintain the function and structure of mitochondrid of liver.

EXAMPLE 14

Effect of SCS on Lower Density Lipoprotein Oxidation

In the present study we reported the effect of SCS on lower density lipoprotein oxidation. The endothelial cells cultured. Fresh human plasma was prepared and LDL was separated with a grads density centrifugation (63000 rpm, 2 h, 1.019<d<1.063). Nitrogen gas and 0.01 mol of SCS added to prevent LDL oxidation. The cells were divided as control group (LDL 1×10–4 mol/L) and treatment Group (SCS group LDL+100 μg SCS/ml). Cell cultured plates were placed in 37° C., $CO_2$ incubated box to incubated for 24 hours.

The data of Table 10 showed that the MDA level of SCS group was lower than that in control group (P<0.01).

TABLE 10

Effects of SCS on bovine aortic smooth muscle cell modified LDL

| Group | MDA (nmol/mg protein, x ± s) |
|---|---|
| Control | 4.50 ± 0.35 |
| Treatment | 2.80 ± 0.29* |

*P < 0.01 compared with control group.

It is known that lower density lipoprotein oxidation caused circulation disease. Lipid peroxidation, for example, induced injury in circulation cells and primary products of lipid peroxidation increased transport of calcium ions. Therefore, decreasing lower density lipoprotein oxidation could prevent and treat circulation disease. The data of Table 14 showed that SCS could significantly decrease MDA. It means that SCS could inhibit oxidative-modified LDL. The inhibited effects of SCS on cell oxidative-modified LDL could help to explain anti-oxidation of SCS.

EXAMPLE 15

Effect of SCS on the Gastrointestinal Protective Effects

The natural of drug Schisandra chinesis Baill has been used for treatment of gastrointestinal disease in China many years. In present study, the effect of SCS on anti-ulcer was examined.
Methods
The experiment of animal was performed as previously described. Mucosal damage in gastrointestinal tract was induced ethanol or indomethacin administration. In ethanol-treated animals, after 24 hours of fasting, ethanol was given orally (70%, v/v, 10 ml/kg) by means of an oral gastric. Mucosal damage was assessed by measurement of areas with hemorrhagic lesion. In the indomethacin ulcer model, rats were refed for 1 hour after 24 hours of fasting. Thirty minutes later, indomethacin (15 mg/kg) was administered subcutaneously and rats were killed 24 hours later. Mucosal lesions were again measured along the greatest diameter. SCS was injected intraperitoneally at doses of 20 mg/kg, one hour before ethanol or indomethacin administration. SCS administration was repeated again 6 hours after indomethacin injection.
Measurement of Myeloperoxidase Activity
After measurement of the lesion areas of the ethanol-treated group, the gastric mucosa was removed by scraping with a glass slide and immediately frozen in liquid nitrogen and stored at −70° C. Myeloperoxidase (MPO) activity assay was based on the o-dianisidine reaction and finally evaluated at 460 nm using a spectrophotometer with horseradish peroxidase as standard.
Results

TABLE 11

Effect of SCS on gastrointestinal mucosal damage

| | Lesion area (mm²) | |
|---|---|---|
| Group | gastric antrum | Small intestine |
| Control | 6.0 ± 0.70 | 425 ± 40 |
| SCS (1) (10 mg/kg) | 2.5 ± 0.35* | 350 ± 38* |
| SCS (2) (25 mg/kg) | 2.0 ± 0.23** | 321 ± 33** |
| SCS (3) (50 mg/kg) | 1.7 ± 0.20** | 295 ± 30** |

*P < 0.01 and **P < 0.001; compared with control group

Oral administration of ethanol induced severe hemorrhagic lesions in the gastric and small intestine mucosa. SCS at doses of 10, 25 and 50 mg/kg dose-dependently reduced the gastric damage. Most effective dose was 50 mg/kg for anti-ulcer action. SCS also reduced the mucosal damage of the small intestine. Above data suggested that SCS could prevent ethanol-induced gastric mucosal damage and indomethacin induced small intestine mucosal damage.

EXAMPLE 16

Effect of SCS on Natural Killer Cell Activity

Animals
Male white Swiss mice, weight about 22–24 g, were used in experiments. Two groups of mice were administered with oral dose of 100 mg/kg (treatment group) or distilled water (control group) every day for two times. One week after the treatment, mice were sacrificed for in experiments.
Cytotoxic T Cell Assay
Briefly, Swiss mice (22–24 g) were used. Spleens from each group were pooled and single cell suspensions were made according to blanden and Langman. Cytotoxicity of the splenic lymphocytes was measured as follows: $5 \times 10^6$ P815 cells in 0.03 ml Eagle's minimum essential medium, which supplemented with 10% hear-inactivated FCS and contained antibiotics, were labeled with 500 $\mu Ci^{51}$ Cr at 37° C. for 1 hour. After labeling, the cells were washed twice with the culture medium and then divided into two equal lots. One lot was infected with influenza virus (15 $EID_{50}$/cell, 1 h at 37° C.) and the other lot used as a control. The target cells were then washed twice and cell concentration adjusted to $1 \times 10^5$ cells/ml. 0.1 ml was distributed into each well of the 96-well tissue culture trays (Linbro Scientific Co.) and 0.1 ml spleen cell suspensions (effector cells) was added (spleen cells were adjusted to $2.5\times10^6$, and $1\times10^7$ cells/ml so that effector/target cells rations were 25:1, 50:1, and 100:1, respectively). The trays were incubated at 37° C. under a gas phase of 10% $CO_2$ in air for 6 h, after which 0.1 ml of the supernatant from each well was removed and radioactivity counted. For total releasable $^{51}Cr$, 2.0 ml of distilled water was added to 0.1 ml target cells and then allowed to stand on the bench for 6 h. This was then spun down and the supernatant was sucked up and radioactivity counted. The percentage specific lysis was calculated as follows:

$$\% \text{ Specific lysis} = \frac{\text{Test culture counts} - \text{spontaneous release counts}}{\text{Water lysis counts} - \text{spontaneous release counts}} \times 100$$

Natural Killer Cytotoxicity Assay

Mice were treated with SCS and virus as described before. Two days after the treatment, spleenic effector cells and target cells were prepared. $^{51}Cr$ release assay was used and the percentage specific lysis was calculated in the same way as mentioned above.

Measurement of Delayed-type Hypersensitivity

Delayed-type hypersensitivity (DTH) in mice was determined by measuring footpad swelling. The animals wee first sensitized by injecting subcutaneously $10^3$ HAU infectious virus diluted in 0.3 ml volume of phosplate-buffer saline (pH 7.3) (PBS). Six days later, each mouse was challenged with 30 μl purified, UV-irradiated virus ($6\times10^3$ HAU), injected into the right hind footpad. The same volume PBS was injected into the left hind footpad as control. It was measured 24, 28 and 72 h after virus challenge with a dial-guage caliper (H. C. Kroplin, Schluchtern, Hessen, Germany) calibrated to 0.05 mm. Results were calculated as follows:

$$\frac{\text{Mean thickness of right hind footpad} - \text{Mean thickness of left hind footpad}}{\text{Mean thickness of normal footpad}} \times 100$$

Anti-hemagglutinin Antibody Assay

The serum anti-hemagglutinin antibody titers were determined by the microtitration hemagglutination-inhibition test.

Briefly, mice in groups of five were bled from the tail veins at different time intervals after immunization with $10^3$ HAU of infectious virus (i.v. injection). The blood was allowed to clot at room temperature. The sera were collected and heat inactivated (56° C., 30 min) to remove nonspecific inhibitors. Two-fold serial dilutions of the immune sera were made with PBS in 96-well round bottom tissue culture trays (Llinbro Scientific Co.) in a final volume of 25 μl. four HAU purified virus in a volume of 25 μl was then added to each well. After 30 min incubation at room temperature, 50 μl of 0.5% fowl erythrocytes was added to all wells and the hemagglutination-inhibition endpoints recorded after a further incubation of about 30 min. The titer of the serum was expressed as the reciprocal of the highest dilution of the serum, which still inhibited the hemagglutination.

Statistical Analysis

Results are expressed as arithmetic mean±standard error of the mean (S.E.M.). Statistical difference for group comparisons was determined by the Student's "t" test.

The data of experiments are summarized in Table 12.

TABLE 12

Effects of SCS on NK cell activity of mice

| | % Specific lysis (mean ± SEM) | | | |
|---|---|---|---|---|
| | RBL-5 | | YAC-1 | |
| Treatment | 50:1 | 100:1 | 50:1 | 100:1 |
| Control | 7.8 ± 8.5 | 15.5 ± 1.5 | 40.5 ± 3.6 | 58.2 ± 6.0 |
| SCS | 12.1 ± 1.2* | 19.8 ± 2.0* | 45.0 ± 3.6* | 64.0 ± 7.1 |

*P < 0.05, significantly different from control group.

The present study aims at evaluating the effects of administration of SCS on the immune function of mice. The results of Table 12 indicated that SCS increased NK cell activity.

EXAMPLE 17

The Effect of SCS on Complement

Complement is a group of normal serum proteins. When the body invades by pathogenic microorganisms, the complement acting together with specific antibodies, exhibits its defensive function. It plays an important role in the anti-infectious immunity of the body.

The methods of animals are similar to previous section.

1. Materials a. Veronal buffer stock:

NaCl 85.00 g, Barbituric acid 5.75 g, sodium barbital 3.75 g. Added 1500 ml of distilled water and heated to dissolve, added distilled water to 2000 ml.

b. 0.1 M $EDTA-Na_3$ stock:

$EDTA-Na_3$ 37.23, NaOH 4.00 g

Added the $EDTA-Na_3$ to 500 ml of distilled water and the NaOH to 100 ml of distilled water. Added it later to the former and $EDTA-Na_3$ would dissolve instantly. Adjusted pH to 7.5 with IN NaOH and added the distilled water to 100 ml.

c. 2% gelatin:

Gelatin 2.0 g added to the distilled water 100 ml and heated to dissolve and stored at 4° C.

d. Gelatin veronal buffer (GVB):

| Veronal buffer stock | 100 ml |
|---|---|
| 0.03 M $CaCl_2$ | 10 ml |
| 0.01 M $MgCl_2$ | 10 ml |
| 2% gelatin | 100 ml |
| Added distilled water to | 1000 ml | e. Alsever solution:

Glucose 20.5 g, NaCl 4.2g, sodium citrate 8.0 g

Dissolved in approximately 800 ml of distilled water and adjusted pH to 6.1 with citric acid. Added distilled water to 1000 ml. Sterilized by autoclaving.

f. 0.01 M EDTA-GVB:

Veronal buffer stock 360 ml, 0.1 M $EDTA-Na_3$ stock 200 ml, 2% gelatin 100 ml,

Added distilled water to 2000 ml.

g. SRBS:

Mixed fresh sterile sheep blood with equal volume of Alsever solution and stored at 4° C. It could be used for several weeks.

h. Hemolysin:
(1) Preparatin of SRBC stroma:
Spun down the SRBC in 1 liter of sheep blood-alsever solution and washed several times with normal saline. Added 10 l. of distilled water which contained 4 ml of glacial acetic acid. Suspended the RBC and put in a 4° C. refrigerator overnight. Discarded the supernatant and packed the settled stroma at 2000 rpm. Suspended the stroma in 0.01 M acetic acid, pH 5.0 and washed 5 times with the acetic acid solution. The acetic acid was then removed and the pH brought to neutral by wash the stroma 3 times each with 0.1 M $Na_2HPO_4$ and normal saline. Packed the stroma by spinning at 7500 rpm. The packed SRBC stroma was then suspended in 300–400 ml of normal saline. Heated to 100° C. for 1 hour. Adjusted with sterile normal saline to 1 mg/ml. Added 0.01% merthiolate and stored at 4° C.
(2) Immunization of rabbits:
Immunized the rabbits by intravenous injections of the SRBC stroma in 2 weeks. Bled the animals 4 days after the last injection. Separated the serum. Inactivated at 56° C. for 30 min and stored at −20° C.
(3) Titration for optimal concentration of hemolysin:
By using 50% hemolysis ($C'H_{50}$) as end-point, SRBC sensitized by various concentrations of hemolysin were titrated agaist various amounts of guinea pig complement. Optimal concentration of hemolysin was determined by $OD_{541}$ reading which gave $C'H_{50}$ and standard curve plotted.

2. Methods
a. Preparation of SRBC suspension—washed SRBC for 5 times with GVB to free from platelets. Filtered to remove cell aggregates. Adjusted the SRBC suspension to $1 \times 10^9$ RBC/ml.
b. Preparation of sensitized SRBC—warmed up 1 volume of hemolysin at the optimal concentration in a 37° C. water bath for 10 min and added equal volume of SRBC suspension at $1 \times 10^9$ cells/ml with stirring. Put in a water bath at 37° C. with shaking for 30 min. Then brought the temperature down in an ice-cool water bath with shaking. Washed the cold SRBC once with 0.01 M EDTA-GVB, twice with GVB and prepared sensitized SRBC suspension at $5 \times 10^8$ cells/ml with GVB.
c. Determination of $CH_{50}$ unit and plotting of standard curves for the serum samples.

Results

The data are summarized in Table 13.

TABLE 13

The effect of SCS on complement

| Treatment | n* | C.P.M. |
| --- | --- | --- |
| Control | 10 | 247 ± 10 |
| Treatment | 10 | 480 ± 51** |

*Number of samples.
**Significant different from virus-infected group; P < 0.01.

Table 13 showed that CPM of T/C is 194.3%. It means SCS increased complement activity. The results of Table 12 and 13 suggested that SCS could increase immune function of mice.

EXAMPLE 18

Effect of SCS on Aflatoxin $B_1$ Induced Liver Cancer

It is known that Aflatoxin $B_1$ can induce liver cancer in rats. In the present study, the effect of SCS on Aflatoxin $B_1$ induced liver cancer was examined.

Methods
Animal

Male rats weighing approximately 200 g were used in this experiment. The rats were housed in polycarbonated cages with hardwood chips with free access to water and diet under controlled conditions of humidity (35 to 55%), lighting (12 hours light-dark cycle), and temperature (24° C.±2° C.). First, the rats were divided into 2 experimental groups. Animals in Group 1 were fed only the basal diet as normal group. Animal in Group 2 were given 300 μg/kg of Aflatoxin $B_1$ by injection (i.p.). Then animal in Group 2 divided into 2 groups. One group treated with SCS (100 mg/kg) by orally as treatment group. Other group was treated with water orally as control group. For the demonstration of iron-excluding liver lesions, prior to killing, 10 animals in each group were iron loaded by injection (12.5 mg/g100 g of body weight, 3 times/week for 2 weeks). Groups of rats were killed at 6, 12, 18, and 24 weeks of treatment.

Histochemistry and Histology

At necropsy, slices from each sublobe of the liver were taken and fixed in 95% cold ethanol for histochemical evaluation of GGT-positive foci and iron-excluding foci and for histological confirmation by hematoxylin and eosin staining. Sections were reacted for GGT and for iron by the blue technique. Determination of the number of profiles of foci and neoplasms was made in serial sections. The number of profiles of foci in each section was counted, and the area of the section was measured to determine the number of profiles/sq cm[37]. The relative iron-excluding area in the liver was determined by the following formula.

$$\text{Relative iron-excluding area in liver} = \frac{\text{Iron-excluding area (sq cm)}}{\text{Whole liver area (sq cm)}} \times 100$$

Bladders were inflated through the urethra by 4% phosphate-buffered formalin and were examined for lesions macroscopically. Tumors and lesions were submitted for histology.

Results

The experimental data show as the following table.

TABLE 14

Effect of SCS of $AFB_1$

| Group | % of iron-excluding area in liver section | Inhibition % |
| --- | --- | --- |
| Normal | 0 | — |
| Control ($AFB_1$) | 18.0 ± 3.0 | — |
| Treatment ($AFB_1$ + SCS) | 2.2 ± 0.2* | 87.8 |

*P < 0.001 Compared with control group

The foci of rat hepatocarcinogenesis were distinguished from surrounding normal liver tissue by a number of phenotypic markers or enzyme-histochemical reaction.

As data of Table 14 showed that $AFB_1$ could markedly induce liver cancer and significantly less and smaller r-GT foci of SCS group than control group. The inhibition rate is 87.8%. It means SCS is effective inhibiting $AFB_1$-induced liver cancer.

EXAMPLE 19

Effect of SCS on DNA Synthesis of Cancer Cells

The present study showed the effect of SCS on DNA synthesis of liver cancer cells.

Methods

The method of animal and liver was described previously. Ascitric hepatoma, S180-v, the transplantable 3924 used. After treatment with SCS (100 mg/kg), rats were injected with [$^3$H]-TdR (10 $\mu$c/$\mu$mole). Two hours after injection the animals were decapitated and examined. Livers and tumors were rapidly removed and blotted on filter paper. Tumors were carefully dissected free of necrotic, hemorrhagic, and nontumorous material. Tissues were minced with sharp scissors and 2 gm. DNA was prepared from the tissues. The radioactivity of the DNA was determined by liquid scintillation counting.

The incorporation of thymidine into DNA ws expressed as cpm/mg of DNA or cpm/gm of tissue.

Results

The data of thymidine incorporation into DNA are shown in Table 15.

TABLE 15

Effect of SCS on DNA synthesis of cancer cells

| Group | [$^3$H]TdR into DNA × 10$^{-3}$ cm/mg | Tissue inhibition rate (%) |
|---|---|---|
| Normal liver | 8.0 ± 0.95 | — |
| Hepatoma C | 20.2 ± 3.0 | — |
| Hepatoma T | 8.8 ± 0.80 | 56.4 |
| S-180 C | 69.5 ± 7.5 | — |
| S-180 T | 39.8 ± 5.2 | 43.2 |
| 3924A C | 87.9 ± 9.6 | — |
| 3924A t | 38.7 ± 4.8 | 52.6 |

The data of table 15 indicated that DNA synthesis of hepatoma, S-180 and 3924A were inhibited by SCS 56.4%, 43.2%, and 52.6%, respectively.

It is known that incorporation [$^3$H]TdR into DNA was low in normal livers, but incorporation was markedly increased in the all liver tumors. Between incorporation of TdR to DNA and grown rate of liver tumors they had good relation. Therefore, [$^3$H]TdR incorporation into DNA could be used measurement of growth rate in liver cancer.

The experimental data showed that SCS markedly inhibited DNA synthesis of liver cancer cells.

EXAMPLE 20

Toxicology Data

A. Acute Toxicity
a. Route of Administration: intravenous and intraperiotoneal injection
   (1) LD$_{50}$ of intraperitoneal injection of the SCS in mice is 1250 mg/kg, and
   (2) LD$_{50}$ of interavenous injection of SCS in mice is 720 mg/kg.
b. Route of administration: the oral route
   LD$_{50}$ of intragastric administration in mice is 5.2 g/kg.
B. The subacute toxicity The subacute toxicity of SCS determined by rats after daily injected administration of SCS over a period of 30 days, baby weight and consumption of food and water were evaluated every day. The subacute toxicity established that by comparison with the control group. Those treated with 500 mg/kg of SCS did not show any differences in consumption of water, food and body weights.

Furthermore the animals had no depressive, excitatory or sleepiness symptoms. Microscopic inspection indicated no alteration in the stomach, liver, spleen and kidneys and in their relative weights.

Additional, after daily administered by intragastric route of 500 mg/kg during 30 consecutive days, the behavior of the animal remained normal, and no abnormalities were found in the liver and kidney function, and histological picture of important organs. The LD$_{50}$ in mice of the intravenous injection is 720 mg/kg, which is more 100 times higher than the dose used in clinical trials for human being. It is obviously to determine the very low toxicity of SCS The World Health Organization (WHO) established the classification of chemicals in 1973, according to relative toxicity. A chemical, which has a LD$_{50}$ of intragastric administration in mice >1 g/kg, is low toxic and >5 g/kg is no toxic. Therefore SCS is a safe natural drug. This low toxicity was confirmed by sub-acute tests and absence of macroscopic lesions of the organ examined.

The preparation of drugs which can be accomplished by the extraction methods set forth above or any conventional methods for extracting the active principles from the plants. The novelty of the present invention resides in the mixture of the active principles in the specified proportions to produce drugs, and in the preparation of dosage units in pharmaceutically acceptable dosage form. The term "pharmaceutically acceptable dosage form" as used hereinabove includes any suitable vehicle for the administration of medications known in the pharmaceutical art, including, by way of example, capsules, tablets, syrups, elixirs, and solutions for parenteral injection with specified ranges of drugs concentration.

In addition, the present invention provides novel methods for regulation of genes of cancer cells with produced safe pharmaceutical agent.

It will thus be shown that there are provided compositions and methods which achieve the various objects of the invention and which are well adapted to meet the conditions of practical use. As various possible embodiments might be made of the above invention, and as various changes might be made in the embodiments set forth above, it is to be understood that all matters herein described are to be interpreted as illustrative and not in a limiting sense.

What is claimed is:

1. A process for producing schisandrin from fruit of *Schisandra chinensis* (Turcz) Baill comprising:
   a. extracting the dried powder of the fruit of *Schisandra chinensis* with boiling water;
   b. filtering the extract of water and obtaining filter residue;
   c. extracting said filter residue with 80% ethanol;
   d. obtaining a residue from the 80% ethanol extract by recovering said ethanol under reduced pressure;
   e. extracting said residue from step d with 80% ethanol-gasoline (1:1);
   f. obtaining a layer of ethanol;
   g. concentrating the ethanol layer;
   h. obtaining a crude crystal under reduced pressure from the concentrated ethanol layer;
   i. dissolving the crude crystal in benzene;
   j. filtering the benzene;
   k. obtaining a residue of benzene by recovering said benzene;
   l. dissolving the residue of benzene in ethanol to obtain a solution of crystalloid material;
   m. drying the solution of crystalloid material to obtain a dried powder;
   n. passing the dried powder through a column packed with Al2O3 and eluting the column using petroleum ether-benzene (1:1) to obtain an elutant;
   o. concentrating said elutant under-reduced pressure to obtain crystals;
   p. recrystallizing the crystals to produces Schisandrin in a crystalline form.

* * * * *